United States Patent
Mahoney et al.

(10) Patent No.: US 6,863,856 B1
(45) Date of Patent: Mar. 8, 2005

(54) SLOTTED MOLD FOR MAKING A CATHETER BALLOON

(75) Inventors: Timothy P. Mahoney, Temecula, CA (US); Michael J. Flick, Lake Elsinore, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/331,851

(22) Filed: Dec. 30, 2002

(51) Int. Cl.[7] .......................... B29C 49/18; B29C 49/64
(52) U.S. Cl. .................. 264/231; 264/235; 264/236; 264/291; 264/296; 264/327; 264/346; 264/347; 264/392; 264/393; 264/519; 264/529; 264/530; 264/534; 264/535; 264/570
(58) Field of Search .......................... 264/231, 235, 264/236, 291, 296, 327, 346, 347, 392, 393, 519, 529, 530, 534, 535, 570; 425/392, 404

(56) References Cited

U.S. PATENT DOCUMENTS

| 5,304,340 | A  | 4/1994  | Downey        |
| 5,522,961 | A  | 6/1996  | Leonhardt     |
| 5,807,520 | A  | 9/1998  | Wang et al.   |
| 6,013,055 | A  | 1/2000  | Bampos et al. |
| 6,117,386 | A  | 9/2000  | Stiger        |
| 6,258,099 | B1 | 7/2001  | Mareiro et al.|
| 6,328,710 | B1 | 12/2001 | Wang et al.   |

*Primary Examiner*—Sandra M. Nolan
(74) *Attorney, Agent, or Firm*—Fulwider Patton Lee & Utecht LLP

(57) ABSTRACT

A method of making a catheter balloon, and a balloon formed thereby, in which a polymeric tube is radially expanded in a mold having a wall with an outer surface and an inner surface defining a chamber, and having at least a section with one or more channels in the wall. The channels result in improved transfer of heat to the polymeric tube within the chamber of the mold during blow molding of the tube to form a balloon, so that the tube is heated more quickly and evenly. One aspect of the invention is directed to a balloon having sections with improved thin walls.

26 Claims, 5 Drawing Sheets

SLOTTED MOLD FOR MAKING A CATHETER BALLOON

BACKGROUND OF THE INVENTION

This invention generally relates to medical devices, and particularly balloon molds for making balloons for intravascular balloon catheters.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

Catheter balloons are typically formed by a blow molding process, in which a polymeric tube is heated and expanded in a mold. The mold has an interior chamber corresponding to the desired configuration of the inflated balloon. The resulting blow molded balloon typically inflates to form an inflated working length, inflated tapering sections on either end of the working section, and proximal and distal skirt sections configured to be attached to the catheter shaft, although conventional balloons may have a variety of configurations depending on the desired use of the balloon catheter. A balloon having a disadvantageously large wall thickness will increase the profile and stiffness of the distal end of the catheter, thus decreasing the maneuverability and crossability (i.e., the ability of the catheter to be positioned across the lesion to be dilated) of the catheter. While considerable development effort has been directed at producing catheter balloons having thinned taper and shaft sections, none of the methods heretofore developed have been completely satisfactory. Prior methods involving removal of balloon material after the balloon is blow molded complicate manufacture of the balloon, and may damage the balloon. Precisely and accurately thinning a section of the balloon to a desired wall thickness has proven difficult. For example, one difficulty has been providing balloon tapered sections having a specific small wall thickness. Thus, it would be a significant advance to provide a catheter balloon and method of making the balloon, having walls with a desired thin wall thickness.

SUMMARY OF THE INVENTION

This invention is directed to a method of making a catheter balloon, and a balloon formed thereby, in which a polymeric tube is radially expanded in a mold having a wall with an outer surface and an inner surface defining a chamber, and having at least a section with one or more channels in the wall of the mold. The channels in the wall of the mold result in improved transfer of heat to the polymeric tube within the chamber of the mold during blow molding of the tube to form a balloon, so that the tube is heated more quickly and evenly. Consequently, the resulting balloon has sections with improved thin walls.

In a presently preferred embodiment, the channel in the wall of the mold has at least a portion which extends through the wall of the mold from the outer surface to the inner surface, so that the portion of the channel extending through the wall is in fluid communication with the interior chamber of the mold. The portion of the channel extending through the wall (i.e., entirely through the wall, from the outer to the inner surface thereof) preferably allows for convective heating of the polymeric tube in the mold chamber. Thus, air introduced into the portion of the channel extending through the mold wall enters the chamber to heat the tube by convection during blow molding of the tube to form a catheter balloon. In an alternative embodiment, the channel extends only partially through the wall, and thus does not provide an opening into the chamber through which air from outside the mold can flow into the chamber of the mold. The channel extending partially through the mold wall preferably improves heat transfer to the tube in the mold chamber, at least in part by reducing the capacity of the wall of the mold to shield the tube from heat applied to the outside of the mold.

In a presently preferred embodiment, the channels comprise slots extending along the wall of the mold, each slot having a length longer than the width of the slot. The slots preferably extend longitudinally (i.e., oriented to a greater degree with the longitudinal axis of the mold than with the circumference of the mold), or, in an alternative embodiment, extend circumferentially around the wall of the mold. In one embodiment, the entire length of the slot extends through the wall of the mold. In an alternative embodiment, the slot has a first portion which extends through the wall and a second portion adjacent thereto which extends only partially through the wall. Depending on the length of the slot, the second portion (i.e., the portion extending partially through the wall) provides radial strength to the slotted section of the mold, so that the tube can be radially expanded in the mold without the slotted section radially expanding. Alternatively, a restraining member can be provided on an outer surface of the mold to prevent the slotted section from radially expanding during expansion of the polymeric tube therein. The embodiment in which the channels in the wall of the mold are slots is generally preferred for providing maximum air flow into the mold chamber. However, in an alternative embodiment, the channels comprises holes extending transversely in the wall of the mold, and preferably a sufficiently large number of holes are present in the wall of the mold to provide a desired amount of air flow into the mold chamber. The holes have a shorter length than the slots, and thus typically provide less air flow into the mold chamber.

In one embodiment, at least the portion of the channel extending through the wall is canted, so that the channel describes a line which does not intersect the center point of the mold inner chamber. The canted channel preferably creates turbulent flow of the heated air, to provide more even convection heating of the tube.

In a presently preferred embodiment, the tube is heated by heating the mold. Thus, the tube is heated by radiative heat from the mold wall, in addition to being heated by convective heat in the embodiment in which at least a portion of the channel extends through the mold wall. In an alternative embodiment, the tube is heated by introducing heated fluid (e.g., heated air or liquid) into an interior of the tube.

The mold chamber typically has a central section, first and second tapered sections at either end of the central section, and end sections at either end of the tapered sections. However, a variety of suitable chamber configurations may be used depending on the desired shape of the balloon. In one embodiment, the channeled section of the mold (i.e., the section of the mold having the channel(s) in the mold wall) extends at least along at least a portion of the central section of the mold. However, the channel can extend along one or both tapered sections and/or one or both end sections either in addition to or instead of extending along the central section of the mold chamber. The tube is typically axially elongated during the blow molding. Preferably, axially elongating the tube during blow molding is facilitated by the channels in the wall of the mold, which provide improved heating of the tube. Thus, in one embodiment, the tube is able to be axially stretched to a greater degree than during blow molding in a mold not having the channels in a wall therein in accordance with the invention. As a result of the axial elongation of the tube in the mold, the portion of the tube heated in a channeled section of the mold is typically at least in part axially stretched into an adjacent section of the mold which may or may not be channeled, and is radially expanded in that adjacent section.

In one embodiment, the polymeric tube is radially expanded in the mold chamber without polymeric material of the tube being molded in the channels in the wall of the mold. Thus, the outer surface of the blow molded balloon is formed by (and corresponds to) the inner surface, of the chamber of the mold, and is not formed by the channels in the wall of the mold. In an alternative embodiment, the polymeric material of the tube is molded in the channels in the wall of the mold, so that the resulting balloon has an outer surface which has raised ridges or other patterns corresponding to the channels in the wall of the mold. The resulting ridges/patterns in the outer surface of the balloon preferably increase the frictional drag of the surface of the balloon for improved stent retention on the balloon or for improved balloon retention in a patient's body lumen during an angioplasty procedure. The size and orientation of the channel in the wall of the mold affects the tendency of the polymeric tube to enter into the channel during blow molding (and thus be molded in the channel). In one embodiment, the channel has a width which is sufficiently small that the polymeric tube is not molded in the channel, and is preferably about 0.004 to about 0.02 inches in width. The width of the channel refers to the smaller transverse dimension of a channel which is in the form of an elongated slot or hole, and to a diameter of a circular hole. Additionally, in the embodiment in which the polymeric tube is not molded in a channel comprising a slot, the slot is preferably longitudinally oriented, as opposed to circumferentially oriented, in order to minimize the tendency of the polymeric tube to be molded in the channel.

One aspect of the invention is directed to a catheter balloon formed according to a method of the invention. A balloon blow molded in a mold in accordance with the invention preferably has an improved thinner wall thickness in one or more desired sections of the balloon. In one embodiment, the blow molding process produces thinned tapered sections and/or shaft sections of the balloon. Specifically, in one embodiment, the balloon has at least one of the proximal and distal tapered sections having at least a portion with a blow molded wall thickness of about 0.0004 to about 0.0006 inches, for a balloon having a working length with an inflated outer diameter (OD) of about 2.9 to about 3.1 mm, and which was preferably blow molded from a uniform diameter polymeric tube having an ID of about 0.019 to about 0.02 inches, and OD of about 0.031 to about 0.032 inches, and a wall thickness of about 0.006 to about 0.007 inches. Similarly, in one embodiment, at least one of the proximal and distal shaft sections of the balloon have at least a portion with a blow molded wall thickness of about 0.002 to about 0.003 inches, and preferably a balloon proximal shaft section with a wall thickness of about 0.002 to about 0.003 inches, and balloon distal shaft section with a wall thickness of about 0.002 to about 0.003 inches. The "blow molded wall thickness" of the balloon refers to the wall thickness produced in the blow molding process without requiring further processing to reduce the wall thickness. Thus, the balloon has thin wall sections formed during the blow molding procedure, and preferably does not require subsequent processing such as necking or physically removing polymeric material to produce the final thin wall thickness of the finished balloon. The thin tapered sections and thin shaft sections of the balloon reduce the profile and increase the flexibility of the distal end of the catheter, for increased maneuverability and crossability. Additionally, in one embodiment, the balloon, which is preferably heated uniformly in a balloon mold which embodies features of the invention, has an improved high burst pressure.

The channeled mold of the invention provides improved transfer of heat energy to the polymeric tube in the interior chamber of the mold, and consequently provides faster, uniform heating of the polymeric tube. Because the tube absorbs the heat more evenly and becomes pliable faster, expansion of the heated material is facilitated, so that the resulting balloon has thinner wall sections than would otherwise be produced from the same polymeric tube blow molded in a convention mold. Moreover, the process time of the blow molding procedure is reduced, thus providing a significant manufacturing advantage. These and other advantages of the invention will become more apparent from the following detailed description of the invention and the accompanying exemplary drawings.

DETAILED DESCRIPTION OF THE INVENTION

Figure 4:
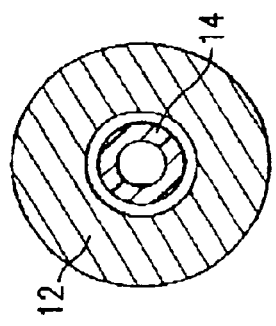
FIGS. 3 and 4 are transverse cross sectional views of the mold assembly shown in FIG. 2, taken along lines 3—3, and 4—4, respectively.
Figure 3:
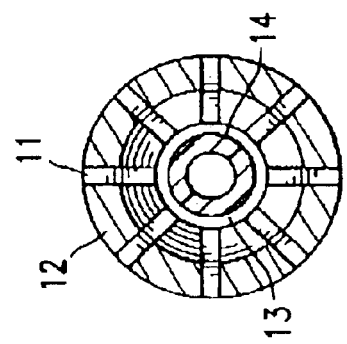
Figure 1:
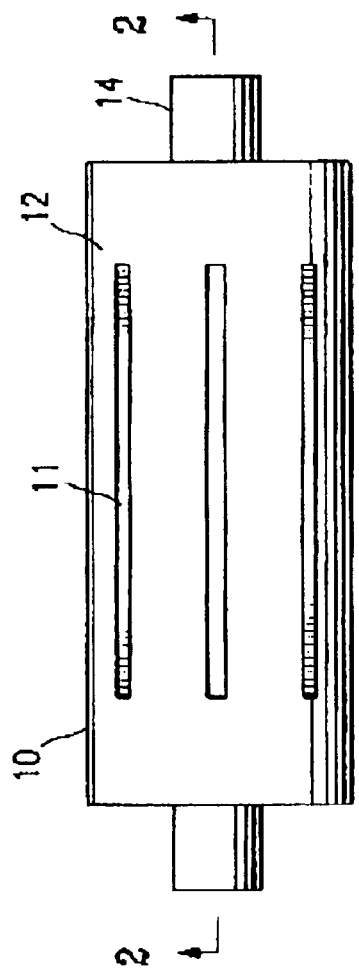
FIG. 1 is an elevational view of a slotted mold embodying features of the invention, illustrating the mold with a polymeric tube in an inner chamber of the mold.
Figure 2:
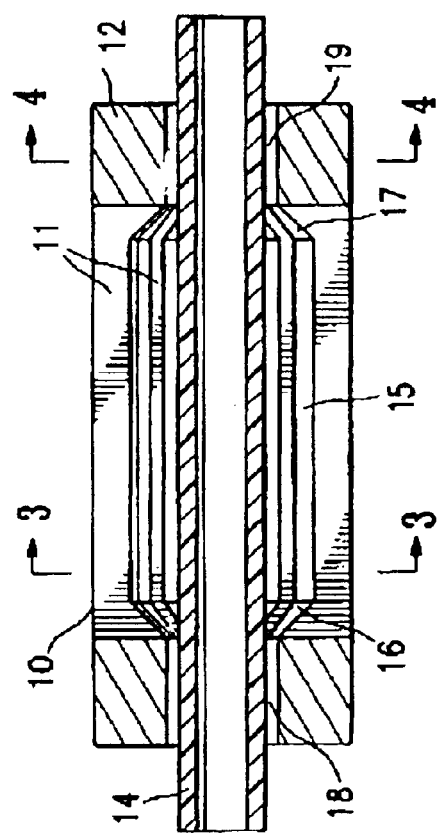
FIG. 2 is a longitudinal cross sectional view of the mold assembly shown in FIG. 1, taken along line 2—2.

FIG. 1 illustrates a mold 10 which embodies features of the invention having channels 11 in a wall 12 of the mold. The mold has an outer surface, and an inner surface which defines an interior chamber 13, as best shown in FIG. 2 illustrating a longitudinal cross section of the mold 10 of FIG. 1, taken along line 2—2, and in FIGS. 3 and 4 illustrating transverse cross sectional views of the mold of FIG. 2, taken along lines 3—3 and 4—4, respectively. A polymer tube 14 is in the mold chamber 13. In the embodiment of FIG. 1, the channels 11 are longitudinally extending slots, the entire length of which extend through the wall 12 of the mold 10 from the outer surface to the inner surface, so that the channels 11 are in fluid communication with the chamber 13, as best illustrated in FIGS. 2 and 3.

The mold chamber 13 has a central section 15, proximal and distal tapered sections 16, 17 at either end of the central section 15, a proximal end section 18 at the proximal end of the proximal tapered section 16, and a distal end section 19 at the distal end of the distal tapered section 17. In the embodiment of FIG. 1, the channels 11 extend along the central section 15 and the tapered sections 16, 17 of the mold chamber 13. However, in alternative embodiments (not shown), the mold 10 has channels 11 extending along at least a portion of one or both of the end sections 18, 19 of the mold chamber 13 in addition to or instead of extending along at least a portion of the other sections of the mold chamber 13. For example, in one preferred alternative embodiment, the mold 10 has channels 13 extending along the tapered sections 16, 17 and the end sections 18, 19 of the mold chamber 13, and not along any of or at least, part of the central section 15, and most preferably not along a central portion of the central section 15.

In the embodiment of FIG. 1, the mold 10 has multiple channels 11 spaced around the circumference thereof, and specifically eight channels 11. However, the number of channels can vary, and is typically about 4 to about 16 for a mold 10 having a central section 15 with a length of about 30 to about 40 mm.

FIG. 1 illustrates the polymer tube 14 in position in the mold 10 for being blow molded to form a balloon for a catheter. In a method of making a balloon for a catheter which embodies features of the invention, the polymer tube 14 is heated in the mold chamber 13, and the heated tube 14 is axially elongated and radially expanded in the mold chamber 13. In a presently preferred embodiment, the tube 14 is heated by heating the mold 10, although depending on the polymeric material forming tube 14, the tube may additionally or alternatively be heated by introducing heated fluid (air or liquid) into the interior of the tube 14 in the mold 10. The mold 10 is formed of a metal such as stainless steel, and the mold 10 is typically heated by a hot air nozzle not in direct contact with the mold 10. As a result of heating the mold 10, the tube 14 is heated by radiative heat from the mold wall and convective heat of heated air from the channels 11 extending through the mold wall 12. The convective heat is the result of heated air which enters the chamber 13 of the mold 10 from the channels 11. The outer opening of each channel is thus unobstructed in whole or at least in part sufficiently to allow the supply of air to enter the channels 11. Preferably, the air entering the channels is the ambient air around the mold 10 which diffuses into the channels, and is naturally drawn into the channels due to convection driven by the internal temperature gradients during the blow molding procedure. Alternatively, a pressurized supply of air forced into the channels 11 may be used if desired (i.e., advection). In the embodiment illustrated in FIG. 1, the channels are perpendicular to a tangent of the outer surface of the mold wall. In an alternative embodiment (not shown), the channels are canted, and preferably at an angle of about 30 to about 70 degrees.

Figure 5:
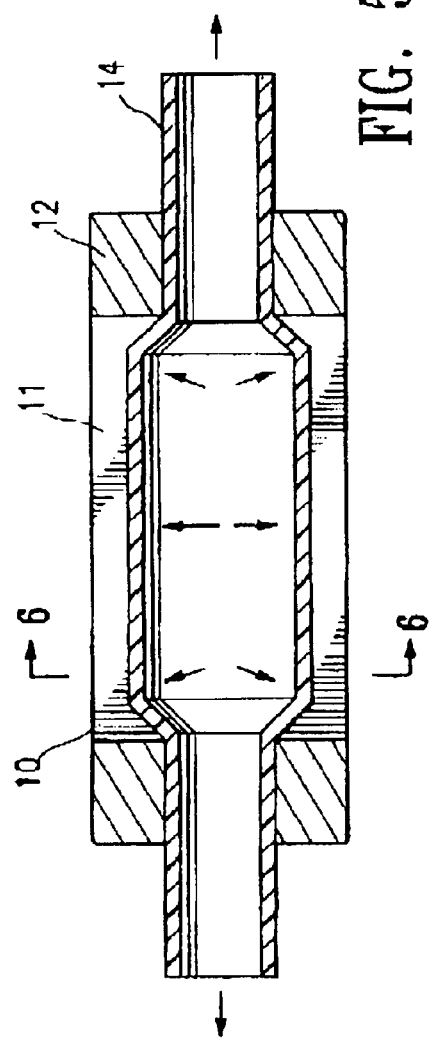
FIG. 5 illustrates the mold assembly of FIG. 2 after the polymeric tube has been axially elongated and radially expanded therein.

The heated polymer tube 14 is axially elongated and radially expanded in the mold chamber 13 by pulling on the ends of the tube 14 and introducing pressurized air into the inner lumen of the tube 14 with one end of the tube 14 blocked off. FIG. 5 illustrates the tube 14 in the mold 10 after the tube is axially elongated and radially expanded therein. The axially elongated tube 14 typically has a length which is about 1 to about 2 times the original length of the tube 14, and a radially expanded diameter corresponding to a blow-up-ratio of about 5 to about 8 (i.e., the ratio of the final radially expanded outer diameter of the tube 14 to the initial unexpanded inner diameter of the tube 14). The thus blow molded tube 14 is cooled to ambient temperature, and deflated and removed from the mold 10, and may be further processed to form a balloon for a catheter.

Figure 7:
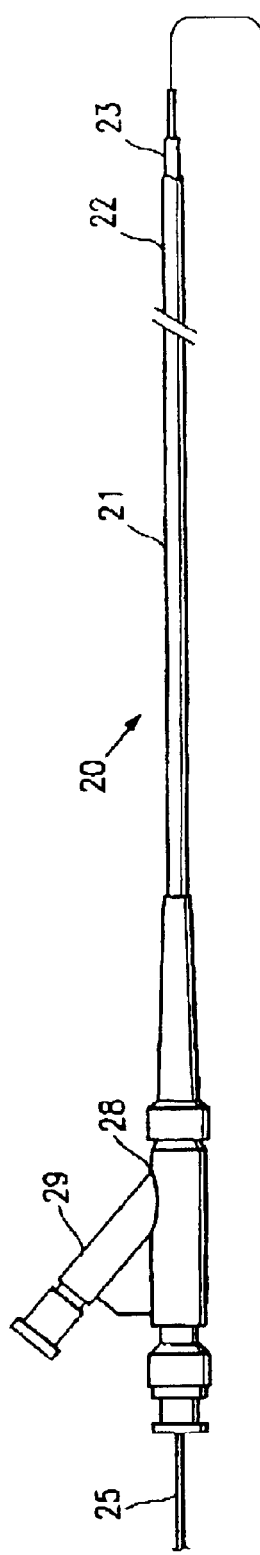
FIG. 7 is an elevational view, partially in section, of a balloon catheter, having a balloon formed according to a method of the invention.
Figure 7:
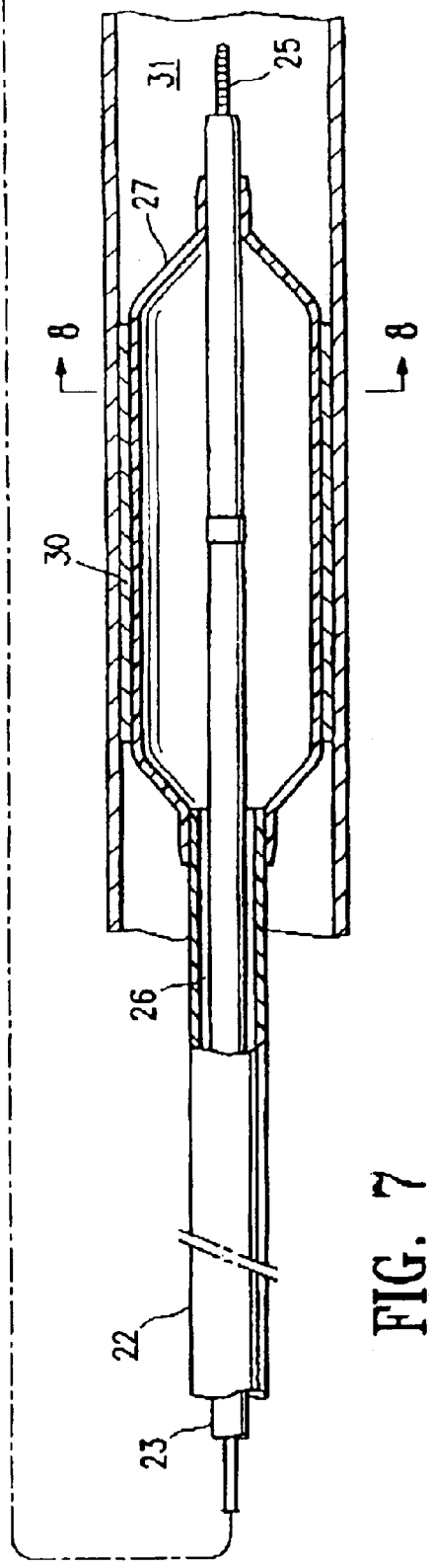
Figure 8:
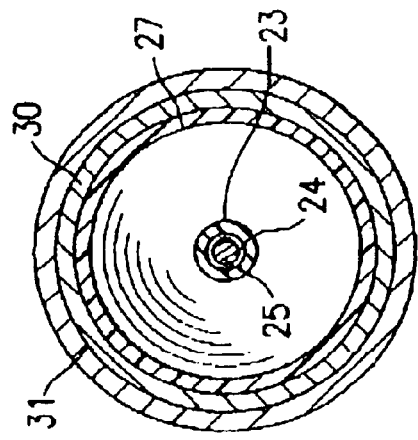
FIG. 8 is a transverse cross sectional view of the balloon catheter shown in FIG. 7, taken along line 8—8.

FIG. 7 illustrates an over-the-wire type balloon catheter 20 having a shaft 21, and an inflatable balloon 27 formed using the mold 10 of FIG. 1. Catheter 20 generally comprises elongated catheter shaft 21 having an outer tubular member 22 and an inner tubular member 23. The coaxial relationship between outer tubular member 22 and inner tubular member 23 defines annular inflation lumen 26. Inner tubular member 23 defines a guidewire lumen 24 configured to slidingly receive a guidewire 25, as best shown in FIG. 8 illustrating a transverse cross section view of the distal end of the catheter shown in FIG. 7, taken along line 8—8. Inflated balloon 27 disposed on a distal section of catheter shaft 21 has an inflated cylindrical working section, inflated tapered sections at either end of the central working section, a proximal skirt section sealingly secured to the distal end of outer tubular member 22, and a distal skirt section sealingly secured to the distal end of inner tubular member 23, so that its interior is in fluid communication with inflation lumen 26. An adapter 28 at the proximal end of catheter shaft 21 is configured to provide access to guidewire lumen 24 and to direct inflation fluid through arm 29 into inflation lumen 26. FIG. 7 illustrates the balloon 27 inflated, with a stent 30 mounted thereon for implanting in a patient's body lumen 31. In use, the distal end of catheter 20 is advanced to a desired region of the patient's body lumen in a conventional manner, and balloon 27 inflated to perform a procedure such as expanding the stent 30 into place in the body lumen, and the balloon deflated for removal of the catheter from the body lumen, leaving the stent 30 implanted therein.

As a result of being axially elongated in the mold chamber 13, the parts of the tube 14 which ultimately form the central inflated working length, the inflated tapered sections at either end thereof, and the skirt sections of the balloon 27 typically have at least a portion thereof heated in a different section of the mold chamber 13 than the section in which it is ultimately radially expanded. Thus, during the axial elongation of the tube 14, the part of the tube 14 located in the slotted tapered sections 16, 17 of the mold chamber 13 during heating of the tube 14 in the mold is stretched into the adjacent end section 18, 19 of the mold chamber 13 and radially expanded therein to form at least a portion of the skirt sections of the balloon 27. Depending on the length of the mold chamber 13 sections, the entire length or only a portion of the part of the tube 14 in the tapered sections 16, 17 of the mold chamber 13 may be stretched into the adjacent end sections 18,19 of the mold chamber 13. Similarly, the part of the tube 14 in the proximal and distal ends of the central section 15 of the mold chamber 13 may be stretched into the adjacent tapered sections 16, 17 or therebeyond and also into the end sections 18, 19 of the mold chamber 13. The preferred extent to which tube 14 is stretched in mold chamber 13 (i.e., the stretch ratio) will vary depending on factors such as the material selection of tube 14. At least a portion of part of the tube 14 heated in the central section 15 of the mold chamber 13 forms the central working length of the balloon 27. Although the resulting balloon 27 illustrated in FIG. 7 has a uniform wall thickness in the inflated configuration, it should be understood that the different sections of the finished uninflated balloon may have different wall thicknesses.

Figure 6:
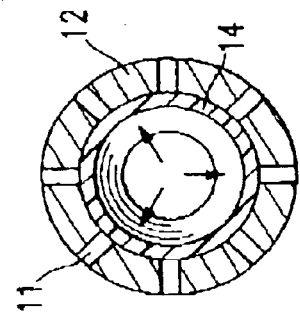
FIG. 6 is a transverse cross sectional view of the mold assembly shown in FIG. 5, taken along line 6—6.

As best illustrated in FIG. 6, in the embodiment of FIG. 1, the dimension and orientation of the channels 11 is such that the polymeric material of the tube 14 remains in the mold chamber 13 and does not enter the channels 1, or at most only slightly enters the channels 11, such that the polymeric material of tube 14 is not molded in the channels 11 during the blow molding. As a result, the balloon 27 has a cylindrical outer surface along the working length thereof with a uniform outer diameter.

Figure 10:
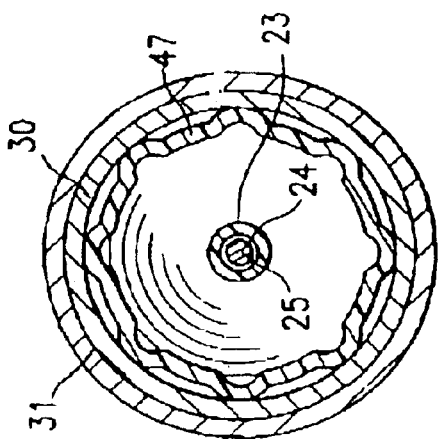
FIG. 10 is a transverse cross sectional view of an alternative embodiment of balloon of the balloon catheter shown in FIG. 7, in which the balloon is formed using the mold shown in FIG. 9, producing ridges on an outer surface of the balloon.
Figure 9:
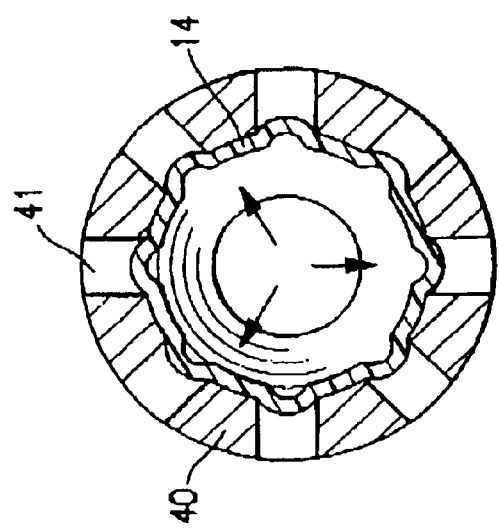
FIG. 9 is a transverse cross sectional view of an alternative embodiment of the mold assembly shown in FIG. 5 with a radially expanded polymeric tube therein, in which the polymeric material of the tube is molded in the channels in the wall of the mold.
Figure 13:
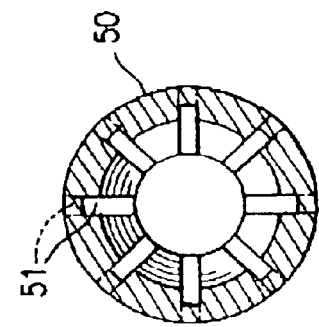
FIG. 13 is a transverse cross sectional view of the mold shown in FIG. 12, taken along line 13—13.

FIG. 9 illustrates a transverse cross section of an alternative embodiment of a mold 40 in which the width of the channels 41 is larger than the channels 11 in the mold 10 of FIG. 6, so that the polymeric material of the tube 14 is molded in the channels 41 of the mold 40 during the blow molding. The channels 41 in the embodiment of FIG. 9 typically have a width of about 0.021 to about 0.05 inches, whereas the channels 11 of the embodiment of FIG. 6 have a width of about 0.008 to about 0.02 inches. FIG. 10 illustrates a transverse cross section of a distal section of an alternative embodiment of catheter 10 having a balloon 47 blow molded in the mold 40 of FIG. 9. Balloon 47 has raised ridges corresponding the channels 41 in the wall of the mold 40 of FIG. 9 so that the outer surface of the balloon 47 has a non-uniform outer diameter along the central inflated working length of the balloon 47.

In the embodiment of FIG. 1, the entire length of the channels 11 extend through the wall of the mold 10. In one embodiment, one or more restraining members (not shown) such as bands or straps are provided around an outer surface of the mold 10 of FIG. 1, to radially restrain the slotted sections of the mold during radial expansion of the polymer tube 14. The restraining members (not shown) are preferably sized to cover only a small amount of the length of the channels 11, and specifically, in one embodiment each restraining member covers about 1% to about 3% of the length of the slots forming channels 11, so that the convective air flow into the channels 11 is not blocked by the restraining members.

Figure 11:
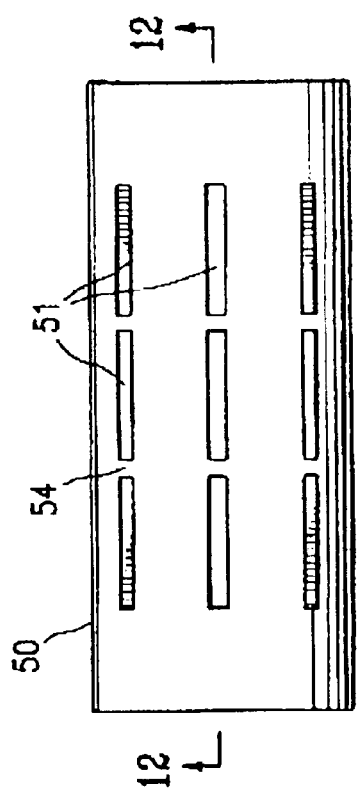
FIG. 11 is an elevational view of an alternative embodiment of a mold, having intermittent portions of the slot extending completely through the wall of the mold separated by portions of the slot which do not extend completely through the wall of the mold.
Figure 12:
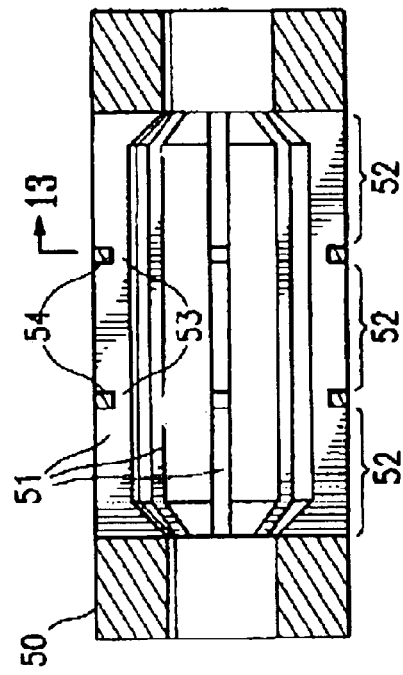
FIG. 12 is a longitudinal cross sectional view of the mold shown in FIG. 11, taken along line 12—12.

FIG. 11 illustrates an alternative embodiment of a mold 50 in which the channels 51 are slots with only a portion of the length of each slot extending completely through the wall of the mold, so that the slot has a first portion 52 which extends through the wall of the mold 50, and a second longitudinally adjacent portion 53 which extends partially through the wall of the mold 50 forming a break in the channel 51, as best shown in FIG. 2, illustrating a longitudinal cross section of the mold 50 of FIG. 11. FIG. 53 illustrates a transverse cross sectional view of the mold 50 of FIG. 12, taken along line 13—13. In the embodiment of FIG. 11, three sections of the channel 51 extending through the wall of the mold 50 are separated by two breaks 54 (i.e., two sections of the wall of the mold 50). However, a variety of suitable configurations may be used with fewer or more breaks 54. In one embodiment, each break 54 in the channel 51 has a length equal to about 1% to about 3% of the total length of the channel 51. In the embodiment of FIG. 11, the break 54 has a depth through the wall of the mold 50 of about 50% of the mold wall, although a variety of depths may be used typically ranging from about 30% to about 80% of the wall of the mold 50. In the embodiment of FIG. 11, the portion of the channel extending partially through the wall of the mold 50 is formed on an inner surface of the mold, so that the channel 51 extends continuously along the inner surface of the mold (albeit only partially though the wall in places along the length of the channel 51), and extends intermittently along the outer surface of the mold 50. In an alternative embodiment (not shown), the portion of the channel extending partially through the wall of the mold 50 is formed on an outer surface of the mold, so that the channel 51 extends continuously along the outer surface of the mold and intermittently along the inner surface of the mold.

Figure 16:
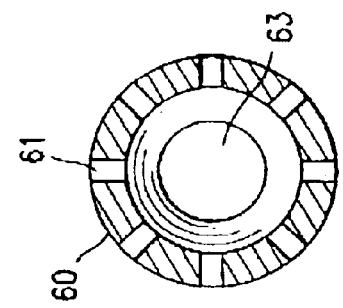
FIG. 16 is a transverse cross sectional view of the mold shown in FIG. 15, taken along line 16—16.
Figure 14:
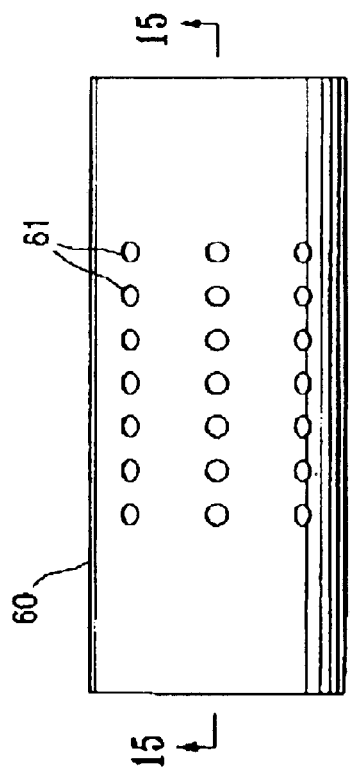
FIG. 14 is an elevational view of an alternative embodiment of a mold, having intermittently spaced holes in the wall of the mold.
Figure 15:
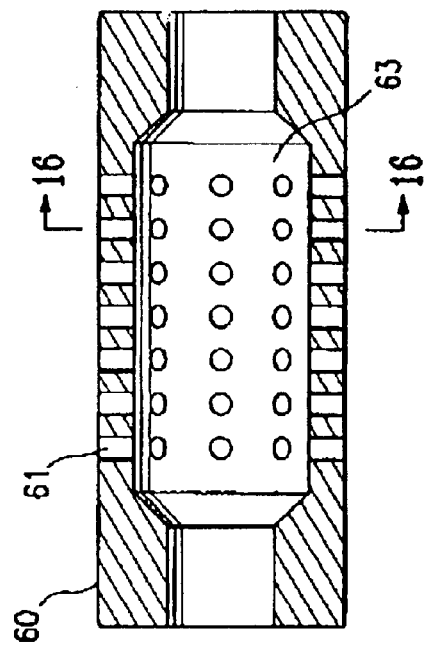
FIG. 15 is a longitudinal cross sectional view of the mold shown in FIG. 14, taken along line 14—14.

FIG. 14 illustrates an alternative embodiment of a mold 60 having channels 61 in the form of intermittently spaced holes. Me holes typically have a diameter of about 0.02 to about 0.05 inches in the embodiment in which the polymeric material of the tube 14 is not molded in the holes 61, to form a balloon with a cylindrical uniform outer diameter along the working length thereof. The holes 61 typically have a diameter of about 0.02 to about 0.06 inches in the embodiment in which the polymeric material of the tube 14 is molded in the holes 61 during blow molding, to form a balloon with raised portions on an outer surface of the working length thereof. Similar to the embodiment of FIG. 1, the holes 61 may be located in one or more of the sections of the mold chamber 63 in addition to or instead of the central section of the mold chamber 63, and the holes may extend in whole or in part through the wall of the mold 60. As best illustrated in FIG. 15 showing a longitudinal cross section of the mold 60 of FIG. 14, taken along line 15—15, the holes 61 extend completely through the wall of the mold 60 from the outer to the inner surface of the mold 60. As best illustrated in FIG. 16 showing a transverse cross section of the mold 60 of FIG. 15, taken along line 16—16, the holes 61 are spaced apart around the entire circumference of the wall of the mold 60. Typically, about 40 to about 60 holes 61 are provided for a mold 60 having a central section 63 which is about 18 to about 20 mm in length.

To the extent not previously discussed herein, the various catheter components may be formed and joined by conventional materials and methods. For example, the outer and inner tubular members 22, 23 can be formed by conventional techniques, such as by extruding and necking materials found useful in intravascular catheters such a polyethylene, polyvinyl chloride, polyesters, polyamides, polyimides, polyurethanes, and composite materials.

The length of the balloon catheter 20 is generally about 108 to about 200 centimeters, preferably about 137 to about 145 centimeters, and typically about 140 centimeters for PTCA. The outer tubular member 22 has an outer diameter (OD) of about 0.017 to about 0.036 inch (0.43–0.91 mm), and an inner diameter (ID) of about 0.012 to about 0.035 inch (0.30–0.89 mm). The inner tubular member 23 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 27 has a length of about 10 mm to about 80 mm, typically about 20 mm to about 40 mm, and an inflated working diameter of about 1.5 mm to about 40 mm, typically about 3 mm to about 10 mm.

While the present invention has been described herein in terms of certain referred embodiments, those skilled in the art will recognize that modifications and improvements may be made without departing form the scope of the invention. For example, although the embodiment illustrated in FIG. 7 is an over-the-wire stent delivery catheter, balloons of this invention may also be used with other types of intravascular catheters, such as rapid exchange balloon catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed:

1. A method of making a catheter balloon, comprising:
    a) placing a polymeric tube in a chamber of a mold, the mold having a wall with an outer surface and an inner surface defining the chamber, and having at least a section with one or more channels in the wall, each channel having at least a portion which extends through the wall from the outer surface to the inner surface so that the portion of the channel is in fluid communication with the chamber;
    b) heating the tube, at least in part by convection heating with air introduced into the portion of the channel extending through the wall; and
    c) radially expanding the heated tube in the mold chamber, to form a catheter balloon.

2. The method of claim 1 wherein the channel comprises a longitudinally or circumferentially extending slot, and b) comprises heating the tube by heating the mold or by introducing a heated fluid into an interior of the tube.

3. The method of claim 2 wherein the slot extends longitudinally along the length of the slotted section of the mold and the entire length of the slot extends through the wall of the mold, and including radially restraining the slotted section of the mold during the radial expansion of the tube with a restraining member around part of the outer surface of the slotted section.

4. The method of claim 2 wherein the slot has a first portion which extends through the wall and a second portion adjacent thereto which extends partially through the wall, and c) comprises radially expanding the tube without radially expanding the slotted section of the mold.

5. The method of claim 1 wherein the mold chamber has a central section, first and second tapered sections at either end of the central section, and end sections at either end of the tapered sections, and the channel extends at least along at least a portion of the central section, and c) includes axially elongating the tube.

6. The method of claim 5 wherein axially elongating the tube comprises stretching the tube so that part of the tube located in the channeled central section of the mold chamber is stretched into the adjacent tapered section of the mold chamber.

7. The method of claim 1 wherein the mold chamber has a central section, first and second tapered sections at either end of the central section, and end sections at either end of the tapered sections, and the channel extends at least along at least a portion of one or both of the tapered sections, and c) includes axially elongating the tube.

8. The method of claim 7 wherein axially elongating the tube comprises stretching the tube so that part of the tube located in the channeled tapered section of the mold chamber is stretched into the adjacent end section of the mold chamber.

9. The method of claim 1 wherein the mold chamber has a central section, first and second tapered sections at either end of the central section, and end sections at either end of the tapered sections, and the channel extends at least along at least a portion of one or both of the end sections, and c) includes axially elongating the tube.

10. The method of claim 2 wherein the slot has a width of about 0.5 to about 1.5 mm, and a length of about 20 to about 40 mm, and the portion of the slot extending through the wall is about 1 to about 3% of the length of the slot, and b) comprises heating the mold so that the tube is heated by radiative heat from the mold wall and convective heat of air from the portion of the slot extending through the wall.

11. The method of claim 2 wherein at least the portion of the slot extending through the wall is canted, and b) comprises heating the mold so that the tube is heated by radiative heat from the mold wall and convective heat of heated air from the canted portion of the slot extending through the wall.

12. The method of claim 1 wherein the channel has a width sufficiently small that polymeric material of the tube is not molded in the channel during c).

13. The method of claim 2 wherein the slot is longitudinally extending along the length of the slotted section of the mold, and the tube is not molded in the slot during c).

14. The method of claim 1 wherein the channel has a width sufficiently large that polymeric material of the tube is molded in the channel during c).

15. A method of making a catheter balloon, comprising:
a) placing a polymeric tube in a chamber of a mold, the mold having a wall with an outer surface and an inner surface defining the chamber, and having at least a section with one or more channels in the wall;
b) heating the tube; and
c) radially expanding the heated tube in the mold chamber without polymeric material of the tube being molded in the wall channels, to form a catheter balloon having a cylindrical outer surface.

16. The method of claim 15 wherein the channels have at least a portion extending through the wall from the outer surface to the inner surface so that the portion of the channel is in fluid communication with the chamber, and b) comprises at least convection heating the tube with heated air from the portion of the channel extending through the wall.

17. The method of claim 15 wherein the channels comprise intermittently spaced holes in the wall, and b) comprises heating the tube by heating the mold or by introducing a heated fluid into an interior of the tube.

18. The method of claim 17 wherein the holes have a diameter of about 0.05 to about 0.2 mm, and including axially elongating the heated tube so that a portion of the tube heated in the section of the mold having the channels is stretched into an adjacent section of the mold.

19. The method of claim 15 wherein the channels comprise slots extending along a length or around a circumference of the slotted section of the mold, each slot having a first portion which extends through the wall and a second portion adjacent thereto which extends partially through the wall, and b) comprises at least convection heating the tube with heated air from the portion of the slot extending through the wall, and including axially elongating the heated tube in the mold.

20. The method of claim 19 wherein radially expanding the heated tube in the mold chamber without the polymeric material of the tube being molded in the wall channels comprises providing each slot with a width sufficiently small that the polymeric material is not imprinted with the shape of the slot, the width being about 0.2 to about 0.5 mm.

21. The method of claim 15 wherein the mold chamber has a central section, first and second tapered sections at either end of the central section, and end sections at either end of the tapered sections, and the section of the mold having the channels extends at least along at least a portion of the central section, and c) includes axially elongating the tube.

22. A method of making a catheter balloon, comprising:
a) placing a polymeric tube in a chamber of a mold, the mold having a wall with an outer surface and an inner surface defining the chamber, and having a central longitudinal section, first and second tapered sections at either end of the central section, and end sections at either end of the tapered sections, the chamber having a diameter which tapers along the tapered sections from the central longitudinal section to a smaller diameter at the end sections, and at least one of the tapered or end sections of the mold having one or more channels which extend at least along at least a portion thereof and which do not extend along the central longitudinal section of the mold, and wherein each channel has at least a portion extending through the wall from the outer surface to the inner surface so that the portion of the channel is in fluid communication with the chamber;
b) heating the tube at least by convection heating the tube with heated air from the portion of the channel extending through the wall; and
c) radially expanding the heated tube in the mold chamber, to form a catheter balloon.

23. A method of making a catheter balloon, comprising:
a) placing a polymeric tube in a chamber of a mold, the mold having a wall with an outer surface, and an inner surface defining the chamber, and having at least a section with one or more channels in the outer surface of the wall which extend only partially through the wall;
b) heating the tube; and
c) radially expanding the heated tube in the mold chamber, to form a catheter balloon having a cylindrical outer surface.

24. The method of claim 23 wherein the mold chamber has a central section, first and second tapered sections at either end of the central section, and end sections at either end of the tapered sections, and the channel extends at least along at least a portion of the central section, and c) includes axially elongating the tube.

25. The method of claim 23 wherein the number of channels in the outer surface of the mold wall is four, and the channels comprise slots extending longitudinally along the outer surface of the mold, and b) comprises heating the tube at least by heating the mold.

26. The method of claim 15 wherein the channels extend only partially though the mold wall, and b) comprises heating the tube at least by heating the mold.

* * * * *

UNITED STATES PATENT AND TRADEMARK OFFICE
CERTIFICATE OF CORRECTION

PATENT NO. : 6,863,856 B1
DATED : March 8, 2005
INVENTOR(S) : Timothy P. Mahoney et al.

It is certified that error appears in the above-identified patent and that said Letters Patent is hereby corrected as shown below:

Column 7,
Line 60, delete "channels 1" and insert -- channels 11 --.

Column 8,
Line 36, delete "Fig. 53" and insert -- Fig. 3 --.
Line 63, delete "Me" and insert -- The --.

Column 9,
Line 43, delete "referred" and insert -- preferred --.
Line 45, delete "departing form" and insert -- departing from --.

Signed and Sealed this

Thirtieth Day of August, 2005

JON W. DUDAS
*Director of the United States Patent and Trademark Office*